United States Patent
Massey et al.

(10) Patent No.: US 9,535,050 B2
(45) Date of Patent: Jan. 3, 2017

(54) FLUID QUALITY MONITORING AND FILTRATION SYSTEM

(71) Applicant: Cummins Filtration IP, Inc., Columbus, IN (US)

(72) Inventors: Jeffrey A. Massey, Cookville, TN (US); Jonathan D. Sheumaker, Cookeville, TN (US); Manish Patel, Greenwood, TN (US); Barry M. Verdegan, Stoughton, WI (US); Matthew L. Schneider, Seymour, IN (US); Venkata Naga Lakshmi Rekha Patchigolla, Columbus, IN (US)

(73) Assignee: Cummins Filtration IP, Inc., Columbus, IN (US)

( * ) Notice: Subject to any disclaimer, the term of this patent is extended or adjusted under 35 U.S.C. 154(b) by 0 days.

(21) Appl. No.: 14/899,717

(22) PCT Filed: Jun. 23, 2014

(86) PCT No.: PCT/US2014/043694
§ 371 (c)(1),
(2) Date: Dec. 18, 2015

(87) PCT Pub. No.: WO2014/209897
PCT Pub. Date: Dec. 31, 2014

(65) Prior Publication Data
US 2016/0139104 A1    May 19, 2016

Related U.S. Application Data

(60) Provisional application No. 61/838,962, filed on Jun. 25, 2013.

(51) Int. Cl.
*B01D 24/00* (2006.01)
*B01D 25/00* (2006.01)
*G01N 15/06* (2006.01)
*G01N 33/00* (2006.01)
*G01N 33/48* (2006.01)
(Continued)

(52) U.S. Cl.
CPC .......... *G01N 33/2888* (2013.01); *F01M 11/10* (2013.01); *G01N 27/12* (2013.01); *G01N 27/22* (2013.01); *F01M 2001/1007* (2013.01); *F16H 57/0405* (2013.01); *F16N 39/06* (2013.01); *F16N 2200/00* (2013.01); *F16N 2200/02* (2013.01);
(Continued)

(58) Field of Classification Search
CPC ......... B01D 24/00; B01D 25/00; G01N 15/06; G01N 33/00; G01N 33/48
USPC  422/68.1, 50, 82.01, 82.02; 436/43; 210/97, 153, 348
See application file for complete search history.

(56) References Cited

U.S. PATENT DOCUMENTS 5,435,170 A   7/1995  Voelker et al.
5,777,210 A   7/1998  Voelker et al.
(Continued)

OTHER PUBLICATIONS

International Search Report and Written Opinion issued for PCT/US2014/043694, Nov. 14, 2014, 10 pages.

*Primary Examiner* — Brian J Sines
(74) *Attorney, Agent, or Firm* — Foley & Lardner LLP

(57) ABSTRACT

A fluid filtration system may include a fluid filter assembly that includes a filter element configured to filter a fluid and a sensor probe incorporated into the fluid filter assembly. The sensor probe may include a chemically reactive material sensitive to at least one property of the fluid and at least a portion of the sensor probe may be exposed to the fluid.

18 Claims, 3 Drawing Sheets

(51) Int. Cl.
*G01N 33/28* (2006.01)
*F01M 11/10* (2006.01)
*G01N 27/12* (2006.01)
*G01N 27/22* (2006.01)
*F01M 1/10* (2006.01)
*F16N 39/06* (2006.01)
*F16H 57/04* (2010.01)

(52) U.S. Cl.
CPC ........ *F16N 2200/08* (2013.01); *F16N 2200/20* (2013.01); *F16N 2250/00* (2013.01)

(56) References Cited

U.S. PATENT DOCUMENTS

| | | |
|---|---|---|
| 5,789,665 A | 8/1998 | Voelker et al. |
| 5,929,754 A * | 7/1999 | Park et al. .................... 340/439 |
| 6,084,393 A * | 7/2000 | Yankielun .................... 324/72.5 |
| 6,553,812 B2 * | 4/2003 | Park et al. ................... 73/54.01 |
| 6,800,194 B1 * | 10/2004 | Stamey et al. ............... 210/96.1 |
| 6,911,141 B2 * | 6/2005 | Stamey et al. .................. 210/85 |
| 7,030,629 B1 * | 4/2006 | Stahlmann et al. .......... 324/663 |
| 7,521,945 B2 * | 4/2009 | Hedges et al. ................ 324/698 |
| 7,928,741 B2 | 4/2011 | Hedges et al. |
| 2003/0085180 A1 | 5/2003 | Akins et al. |
| 2005/0066711 A1 | 3/2005 | Discenzo |
| 2005/0126983 A1 | 6/2005 | Maxwell et al. |
| 2009/0230063 A1 | 9/2009 | Hawkins et al. |
| 2010/0319331 A1 | 12/2010 | Wagner et al. |

* cited by examiner

FLUID QUALITY MONITORING AND FILTRATION SYSTEM

CROSS REFERENCE TO RELATED APPLICATIONS

This application is a National Stage of PCT Application No. PCT/US2014/043694, filed Jun. 23, 2014, which claims priority to and the benefit of U.S. Provisional Patent Application No. 61/838,962, filed Jun. 25, 2013. The contents of both applications are herein incorporated by reference in their entirety and for all purposes.

FIELD

This technical disclosure relates to monitoring fluid quality in a fluid filtration system.

BACKGROUND

Oil drain intervals for internal combustion engines are determined by engine manufacturers through rigorous testing. However, a manufacturer cannot simulate all the conditions under which an engine can subject the lubricating oil to. Determining the quality of the in-service lubricating oil in-situ would provide a more accurate assessment of when the oil should be changed. In addition to assessing quality, assessing oil chemical constituents of the in-service lubricating oil in-situ would be useful.

Similarly, the reliability and/or performance of high pressure common rail diesel fuel injection systems may be adversely impacted by the presence of certain contaminants in the fuel, such as water. Typically, the end user would not be aware of the presence of these contaminants until engine performance has been impacted. As such, the ability to detect the presence of contaminants and advise the operator or service personnel accordingly is desirable.

A polymeric bead matrix (PBM) sensor probe is a known type of sensor used to sense the quality of a fluid such as oil. Examples of PBM sensor probes and how they work are described in U.S. Pat. Nos. 5,435,170; 5,777,210; 5,789,665; 7,521,945; and 7,928,741. It is known to use PBM sensors on oil sumps in engines.

SUMMARY

Various embodiments provide a system and method wherein a disposable sensor probe is incorporated into a fluid filter assembly, including but not limited to a lubrication oil, hydraulic fluid or fuel filter assembly. The sensor probe can be designed to sense the quality of the in-service fluid in-situ, and also can provide the ability to assess chemical or contaminant constituents of the fluid thereby providing information that can be used to, for example, to determine fluid or filter service intervals.

The fluid can be any fluid that one wishes to monitor the quality of including, but not limited to, oils such as lubrication oil, hydraulic fluid, turbine oil, gear oil, compressor oil, transformer oil, fuel such as diesel fuel, water, engine coolant, glycol and amine-based fluids and ester-based fluids, and other liquids. The fluid can be used in an engine, for example a diesel engine, a hydraulic system, or in any other fluid system.

The sensor probe can be suitably integrated into a fluid filtration system having a fluid filter assembly that includes a disposable filter element. In one embodiment, the sensor probe can be integrated or installed into the fluid filter assembly, such as the disposable filter element, the filter head, a filter housing, a standpipe, the sump, an engine lubricating fluid circuit, or other filter components. According to another embodiment, the sensor probe may be incorporated into a centrifuge cartridge. The sensor probe can be in electrical communication, wired or wirelessly, with a suitable controller, such as an engine control module/unit (ECU) or other device utilizing a signal processor, which in turn provides an output indicative of the quality of the fluid being filtered.

In one embodiment, the sensor probe can be integrated into the disposable filter element, such as a lube oil, hydraulic fluid, turbine oil, gear oil, compressor oil, or fuel filter element. When the sensor probe is an integral part of the disposable filter element, replacement of the sensor probe can be simply accomplished by changing the filter element.

In one embodiment, the sensor probe can be integrated into other elements of the fluid filter assembly such as the filter head, the housing, the standpipe, or other filter components. In this embodiment, replacement of the sensor probe may be a separate action from servicing of the disposable filter element, but may occur at the same time that the disposable filter element is serviced.

A sensor probe as used in this disclosure and claims is defined, unless otherwise indicated by the applicant, as any type of sensing device that employs chemically reactive material(s) and may therefore be sensitive to certain properties (e.g. a chemical concentration, a contaminant concentration, or a fluid parameter) of the fluid being filtered. For example, at least one electrical property of the chemically reactive material(s) may temporarily or permanently change upon exposure to certain properties, such as a chemical or contaminant species of interest, of the fluid being monitored. The changes in the electrical property may indicate at least one of the fluid quality, the fluid chemistry, or the chemical composition of the fluid. According to one embodiment, the sensor probe may return to its base condition after a period of time or after certain processing. One example of a sensor probe that can be used includes, but is not limited to, a PBM sensor probe that employs chemically reactive polymeric bead(s) disposed in a space between two electrodes, such as an inner and an outer electrode. The PBM sensor probe can have a construction as described herein, or described in U.S. Pat. Nos. 5,435,170; 5,777,210; 5,789,665; 7,521,945; and 7,928,741, or other constructions employing chemically reactive polymeric beads and that are capable of sensing fluid quality and/or assess chemical constituents of the fluid. Alternatively or additionally, the sensor probe may use an inorganic or non-polymeric material, such as zeolite, that may respond to changes in fluid quality and/or chemical constituents.

Fluid quality, as the term is used in this disclosure and claims, is defined, unless otherwise indicated by the applicant, as any property or parameter or combination of parameters or properties of a fluid being monitored that is measurable by the sensor probe as a result of a temporary or permanent change in the electrical properties of the sensor probe upon exposure to certain properties, such as the chemical or contaminant species of interest, of the fluid being monitored or filtered. In the case of lube oil applications, one example of fluid quality includes, but is not limited to, the oil acidity or a specific oil additive. In the case of fuel applications, one example of fluid quality includes, but is not limited to, the concentration of water or sulfur in the fuel. Alternatively or additionally, the fluid quality may include at least one of a soot level, fuel concentration, water concentration, or an extent of at least one of additive depletion, fluid oxidation, nitration, thermal degradation, liquid contamination, solid contamination, or semi-solid particulate contamination.

A single sensor probe or multiple sensor probes can be provided. The single sensor probe can be designed to sense a single quality characteristic or chemical constituent of the fluid, or the sensor probe can be designed to sense a plurality of quality characteristics and/or chemical constituents of the fluid. If multiple sensor probes are used, each probe can sense a different quality characteristic or chemical constituent of the fluid or one or more of the probes can be designed to sense a plurality of quality characteristics and/or chemical constituents.

In the case of lube oil, many oil quality monitoring and sensing technologies can be intended to last the life of the engine. As such, they tend to be more expensive and outlast the typical service interval of a fluid filter. On the other hand, a sensing probe described herein can provide more data with regards to more specific oil quality measures. According to one embodiment, the sensing probe may be disposable and may undergo a permanent change in its electrical properties. Thus, the sensor probe may be regularly replaced with, for example, the filter element or when an oil change occurs, and the sensor probe may further provide more useful fluid quality data at a low cost. According to one embodiment, the sensor probe must be replaced with the filter element due to the configuration and properties of conventional sensor probes.

In addition, by having the sensor probe installed with the filter element, the sensor probe may be changed at each oil change and/or when the filter is changed. With the current technology platforms, both the oil sensor and filter may be changed independently, requiring multiple maintenance steps in replacing the consumable components. With the sensor probe described herein installed with the filter element, the multiple maintenance steps can be reduced to a single maintenance step creating a more efficient maintenance procedure. Additionally, the consumer may only have to purchase one replaceable part (i.e. the filter element and integrated sensor probe), rather than multiple replacement parts at each oil change.

The result of having a single consumable part (e.g. the filter element and the integrated sensor probe) has an additional advantage in the design and cost of the sensor probe and ensures that the sensor probe is replaced. If the sensor probe were to remain separate from the oil filter element, then the potential oversight of maintenance workers to replace the probe during an oil change would require that the probe be structurally designed to withstand the resulting increased service life of the sensing probe. Additionally, the oil quality monitoring system may become unreliable if the probe is not replaced each oil maintenance interval. However, by integrating the sensor probe with the filter element (thus ensuring changing at each maintenance interval), the design of the sensor probe can be optimized for the decreased in-service life, which may result in a decreased material and manufacturing cost of the probe. Also, integrating the sensor probe with the filter element may ensure that the sensor probe's impact on the fluid quality monitoring system's reliability is enhanced.

In addition to the previously discussed advantages, integrating the sensor probe with the disposable filter element can further provide a means of protecting engines and equipment by ensuring that appropriate filtration is being used. Filter elements that lack the integrated sensor probe may not produce a recognizable electrical signal to the controller, enabling recognition that an inappropriate filter element is being used. This could be used to alert the operator accordingly or to adapt the fluid quality diagnostics for operation in a mode to mitigate damage to the engine caused by improper filtration.

Various embodiments provide for a fluid filtration system including a fluid filter assembly that includes a filter element configured to filter a fluid and a sensor probe incorporated into the fluid filter assembly. The sensor probe may include a chemically reactive material sensitive to at least one property of the fluid and at least a portion of the sensor probe may be exposed to the fluid.

Another embodiment provides for a filter element that may include filtration media suitable for filtering a fluid and a sensor probe arranged relative to the filtration media so as to be in contact with the fluid prior to or after being filtered by the filtration media. The sensor probe may include a chemically reactive material whose electrical properties change according to at least one property of the fluid, and the sensor probe may be disposable with the filtration media. The sensor probe may also include identifying information regarding the filter element.

Yet another embodiment provides a method of monitoring a fluid within a fluid filter assembly. The method may include integrating a sensor probe into a filter element of the fluid filter assembly and exposing the sensor probe to the fluid. The sensor probe may include a chemically reactive material whose electrical properties change as a result of at least one property of the fluid being filtered.

These and other features (including, but not limited to, retaining features and/or viewing features), together with the organization and manner of operation thereof, will become apparent from the following detailed description when taken in conjunction with the accompanying drawings, wherein like elements have like numerals throughout the several drawings described below.

DRAWINGS

DETAILED DESCRIPTION

As described further below and referring to the figures generally, the various embodiments disclosed herein related to systems and methods where a sensor probe may be incorporated into a fluid filter assembly. The sensor probe may sense the quality of the in-service fluid in-situ, and may also assess the chemical constituents of the fluid thereby providing information that can be used to, for example, tailor chemical additives to be added to the fluid and/or to determine when it is time to service the filter and/or the fluid.

A fluid filtration system is defined herein as a system that includes the fluid filter assembly and other components such as fluid flow lines and an engine or other system that utilizes the fluid.

The fluid filter assembly can be any assembly that is used to filter a fluid including, but not limited to, a lubrication oil, hydraulic fluid, or fuel filter assembly. The fluid can be any fluid that one wishes to monitor the quality of including, but not limited to, lubrication oil, hydraulic fluid and fuel such as diesel fuel. The fluid can be used in an engine, for example a diesel engine, a hydraulic system, or in any other fluid system.

Figure 4:
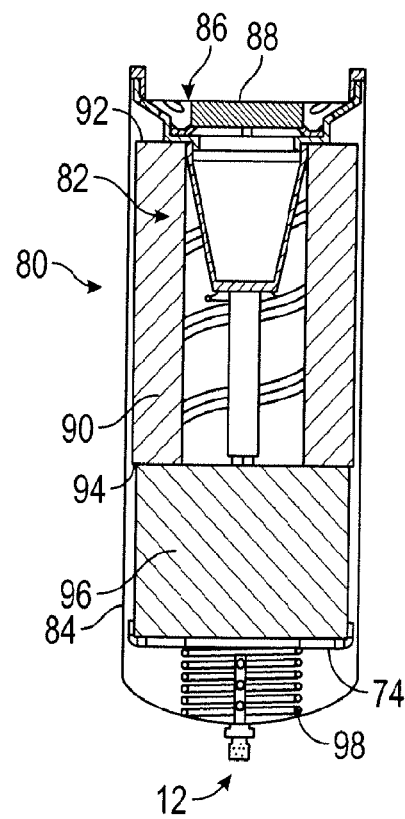
FIG. 4 illustrates a sensor probe incorporated into one embodiment of a spin-on filter element.
Figure 5:
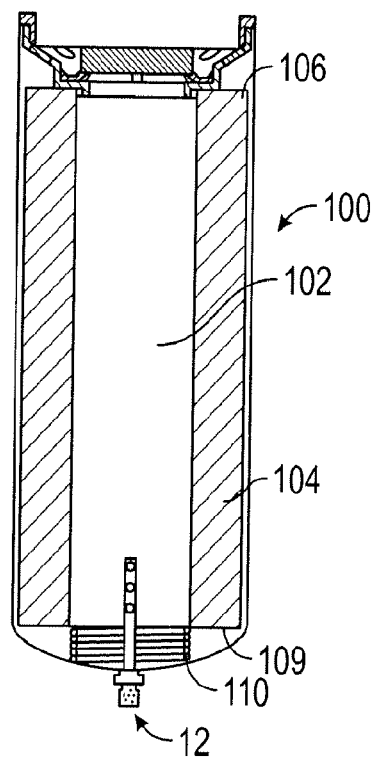
FIG. 5 illustrates a sensor probe incorporated into another embodiment of a spin-on filter element.

A fluid filter assembly is defined herein as including a disposable filter element, a filter head to which the disposable filter element is attached, a filter housing, an optional standpipe that is part of the filter housing and over which the disposable filter element is installed, or optional additional filter components. The fluid filter assembly may be, for example, a cartridge-style filter in which the filter element (or filter element cartridge) may be removed from the filter housing and replaced separately from the filter housing. Alternatively, the fluid filter assembly may be, for example, a spin-on filter (as shown in FIGS. 4 and 5) in which the filter housing may contain the filter element and both the filter housing and element may be removed, disposed of, and replaced at the same time. Accordingly, the disposable filter element can be, for example, a disposable filter element cartridge that is removably installed within a filter housing during use, or a disposable spin-on type filter element where the filter media is disposed within a filter housing and the filter media and filter housing are disposed of together.

A filter element is defined herein as any disposable filter suitable for filtering a fluid, where the disposable filtration media has an upstream or unfiltered fluid side and a downstream or filtered fluid side. The filter element may use, for example, filtration media or a fibrous material to remove at least one contaminant. The filter element may optionally include at least one endcap, a center tube, a housing, and/or a nutplate. The fluid to be filtered flows from the upstream side to the downstream side through the filtration media which filters the fluid. The filtration media can be arranged in any configuration including, but not limited to, a ring or a panel. The filtration media can be removable from a filter housing and disposed of, such as cartridge filter elements. The filtration media can also be disposed (optionally) permanently, within a housing, where both the filtration media and the housing are disposed of, such as in a spin-on filter element.

The sensor probe can be suitably integrated anywhere in the fluid filtration system. In one embodiment described in detail below, the sensor probe is integrated into the fluid filter assembly, particularly the disposable filter element. When the sensor probe is an integral part of the disposable filter element, replacement of the sensor probe is simply accomplished by changing the filter element, which may, according to various embodiments, be attached to other components within the fluid filter assembly. However, the sensor probe may be integrated into other elements of the fluid filter assembly, such as the filter head, the housing, the standpipe, the nutplate, the filter housing, or other non-filter element or filter components. Therefore, the sensor probe may be replaced separately from servicing the disposable filter element. Replacing the sensor probe may optionally occur at the same time the disposable filter element is serviced.

According to another embodiment, the sensor probe may be incorporated into a centrifuge cartridge. For example, the sensor probe may be integrated with centrifuges commonly known as "ConeStaC™" or "SpiraTec™" centrifuges, which may be disposable or incinerable. The ConeStaC™ centrifuge may allow fluid flow to pass through gaps between a cone stack, which may reduce the distance for the particles to travel to be captured and may therefore increase efficiency. The SpiraTec™ centrifuge or rotor may increase the separation efficiency by reducing the distance the contaminated fluid must travel within the rotor before separating and sending clean oil back to the sump. More specifically, the SpiraTec™ centrifuge may allow fluid to pass through gaps between spiral vanes, which guide the contamination outward to the rotor perimeter where the G-forces are highest. The contamination may collect on the inside rotor wall.

The sensor probe may be situated upstream or downstream of the filter element. For example, a sensor probe that is downstream of the filter media may indicate that a fuel-water separator has failed. Alternatively or additionally, a sensor probe located upstream of the filter media may indicated that the operator has received a shipment of poor quality fuel (e.g. fuel containing excessive amounts of water).

Figure 1:
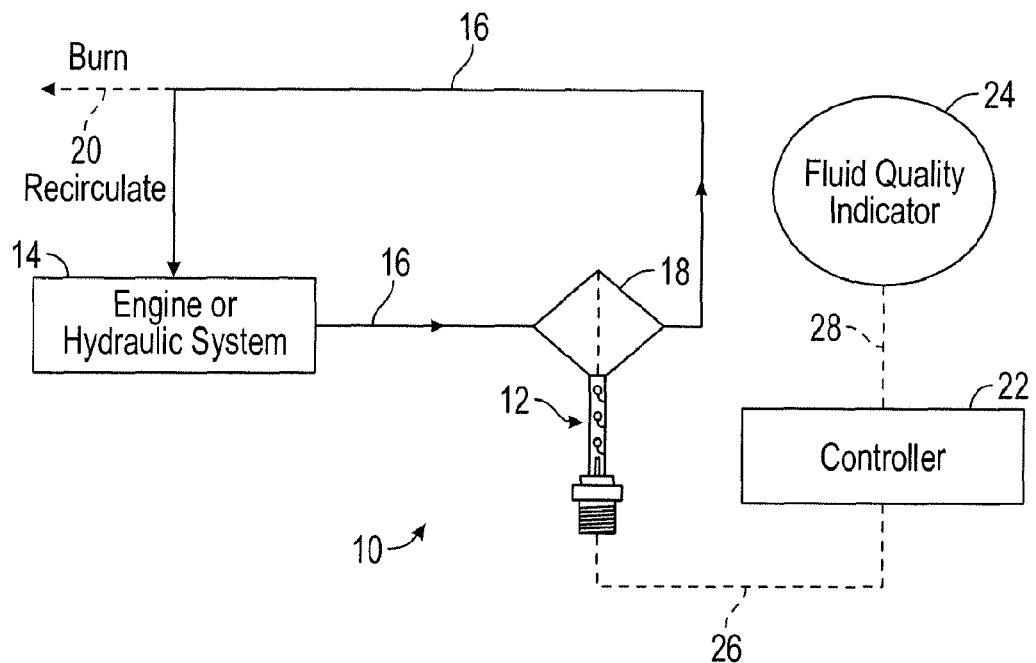
FIG. 1 is a schematic depiction of a fluid filtration system that incorporates a disposable sensor probe according to one embodiment.

FIG. 1 is a schematic depiction of a fluid filtration system 10 that incorporates a disposable sensor probe 12. In the illustrated example, the system 10 is shown as being part of an engine or hydraulic system 14 and supplies a fluid, such as lube oil, fuel or hydraulic fluid to the engine or hydraulic system 14 along fluid flow lines 16. In this example, the sensor probe 12 is shown as being integrated into a fluid filter assembly 18 that is fluidly connected in the flow lines 16 to filter the fluid flowing through the flow lines before the fluid is directed to the engine or hydraulic system 14.

In the case of lubrication and hydraulic systems, the lube oil or hydraulic fluid is recirculated in a closed flow path. In a fuel system, typically some of the fuel is burned in the combustion process as shown by the dashed line 20 and some fuel is recirculated. The sensor probe 12 produces an electronic output or electrically communicates, via wires or wirelessly, with a suitable controller 22 (as shown by dashed line 26), such as an engine control module/unit (ECU) or other signal processor, which in turn provides some form of an indicator or output 24 indicative of the quality of the fluid being filtered (which may be transmitted through a variety of means and is shown with dashed line 28). The output 24 can be in any form including, but not limited to, a visual signal, an audible signal, a numerical value, an indicator on a gauge, a controlled, automatic release of additive into the fluid, and any combination thereof.

The sensor probe 12 can be any type of sensing device that employs chemically reactive material(s) whose electrical properties may temporarily or permanently change upon exposure to a property, such as a chemical or contaminant species or element of interest, in the fluid being monitored. According to one embodiment, the sensor probe may return to its base condition after a period of time or after certain processing. According to one embodiment, in the case of the fluid being lubrication oil and where one is interested in monitoring the acidity of the oil or a specific oil additive, the electrical properties of chemically reactive material(s) in the sensor probe may undergo a temporary or permanent change when exposed to the acids or the oil additive, if present in the oil. Similarly, according to another embodiment in the case of the fluid being fuel and where one is interested in monitoring the concentration of water in the fuel, the electrical properties of chemically reactive material(s) in the sensor probe may undergo a temporary or permanent change when exposed to the water, if present in the fuel. The change in the electrical properties of the sensor probe 12 may be communicated to the controller 22.

Figure 2:
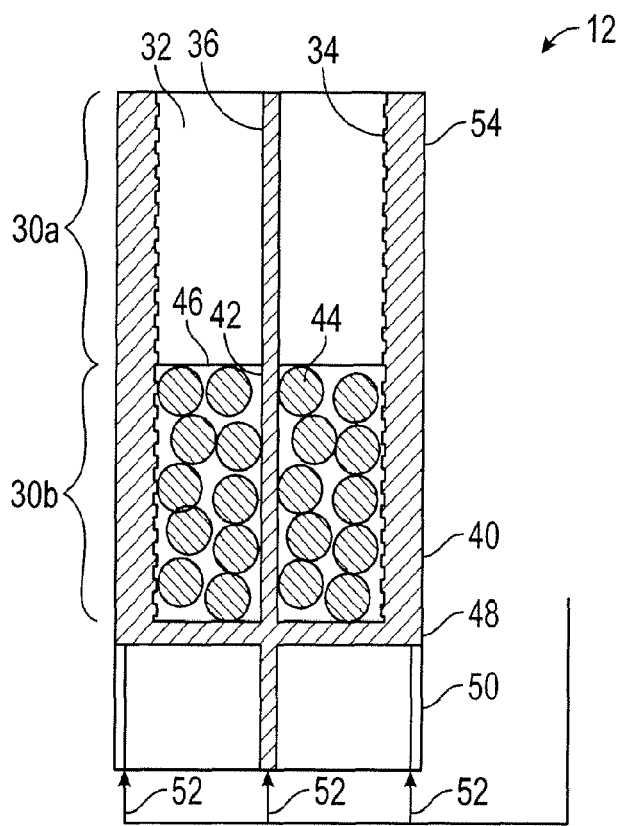
FIG. 2 is a simplified schematic cross-sectional view of one embodiment of a sensor probe that can be used.

According to another embodiment, the sensor probe 12 may include a PBM sensor probe that employs chemically reactive polymeric bead(s) disposed in a space between two electrodes, such as an inner and an outer electrode. Instead of or in addition to polymeric beads, water absorbing hydrogels, zeolties, silica, or other inorganic or non-polymeric material that responds to specific chemical changes, species, or elements may be used. For example, the polymeric beads could be replaced by a superabsorbent hydrogel, silica or clay in order to detect water in fuel. A schematic depiction of the basic features of a PBM sensor probe that can be used is shown in FIG. 2. The PBM sensor probe can have constructions other than that shown in FIG. 2. Additional information on the construction and operation of PBM sensor probes can be found in U.S. Pat. Nos. 5,435,170; 5,777,210; 5,789,665; 7,521,945; and 7,928,741, which are incorporated herein by reference in their entirety. However, sensor probes other than PBM sensor probes can be used.

In FIG. 2, the probe 12 is generally cylindrical in construction and includes two sensing chambers 30a, 30b making up the sensing portion of the probe. In the first or upper chamber 30a, a space 32 is defined between a first perforated, cylindrical outer electrode 34 and a first inner or central electrode 36 that is surrounded by the electrode 34. In use, the PBM sensor probe may be connected to the fluid filtration system such that the fluid can at least partially fill the space 32, and the conductance or polarity of the fluid filled space 32 between the electrode 34 and the electrode 36 is measured.

In the second or lower chamber 30b, a space 38 is defined between a second perforated, cylindrical outer electrode 40 and a second inner or central electrode 42. The electrode 42 could be separate from the electrode 36, or the electrodes 42 and 36 can be integrally formed with each other. Polymeric beads 44 may fill the space 38. In use, the fluid fills the voids between the polymeric beads 44 in space 38, and the conductance or polarity of the fluid and polymeric bead filled space 38 between the electrode 40 and the electrode 42 is measured.

According to another embodiment, the sensor probe 12 may condition and compare the signals or conductance of the electrodes and the controller 22 may not be required to measure the conductance.

The two chambers 30a, 30b may be separated by an insulator 46, and an insulator 48 may be disposed between the chamber 30b and a mounting protrusion 50 that aids in mounting the PBM sensor probe. The various electrodes 34, 36, 40, 42 are electrically connected via wires or other means to electrical connectors 52 in the mounting protrusion for electrically connecting the PBM sensor probe to the controller 22. All of the components are housed within a housing 54. The probe 12 may also be configured to allow fluid to penetrate into the interior spaces 32, 38. For example, this can be achieved by making some or all of the housing 54 permeable to the fluid, such as by providing perforations in at least the upper portion of the housing 54 or making the material that forms the upper portion of the housing 54 generally freely permeable to the fluid. Fluid may also be allowed to flow in and/or out via the upper tip end of the probe 12, such as through a permeable or apertured structure at the upper tip end. In such cases, it may also be desirable for insulator 46 to be a permeable or apertured structure to facilitate fluid entry to chamber 30b.

By comparing at least one of the conductivity or capacitance across the two chambers 30a, 30b, a characteristic of the fluid or fluid quality parameter can be determined. Alternatively or additionally, at least one of the conductivity or capacitance across one of the chambers 30a or 30b may be used as a fluid quality parameter. The electrical properties of the polymeric beads 44 may temporarily or permanently change when the beads 44 are exposed to the requisite chemical or contaminant constituents of interest present in the fluid being monitored. The differential conductivity (or capacitance) between the two or more chambers 30a, 30b may be indicative of the condition of the fluid. This can be used to determine when to change the fluid, sensor and filter, for recirculating fluid systems such as lube or hydraulic oil systems. For fuel systems, this can be used to prompt corrective action by service or other personnel, such as changing the filter and sensor, the addition of fuel additives to the fuel, etc.

The sensor probe 12 can be formed with multiple chambers containing polymeric beads or other sensing materials that respond to different chemical or contaminant constituents or that are shielded from exposure to certain chemical or contaminant species in the fluid. This would enable the sensor probe to monitor different properties of the fluid. Alternatively, multiple sensor probes 12 can be provided, each of which is designed to monitor different chemical or contaminant species or different properties of the fluid In the example illustrated in FIG. 2, the outer electrode 34 can be integrally formed with the outer electrode 40 so that they form a single, unitary, one-piece construction, and/or the electrode 36 can be integrally formed with the electrode 42 so that they form a single, unitary, one-piece construction. However, the electrodes can be formed separately from one another. Further, if the two pairs of electrodes (e.g. electrode 34 and 40 and/or electrodes 36 and 42) each form a single, unitary, one-piece construction, the two pairs of electrodes may be electrically isolated from one another and measured separately.

As discussed above, it may be advantageous to integrate the sensor probe 12 into the disposable filter element because replacement of the sensor probe may be accomplished by changing the filter element. The sensor probe 12 can be integrated into any type and form of disposable filter element.

Figure 3:
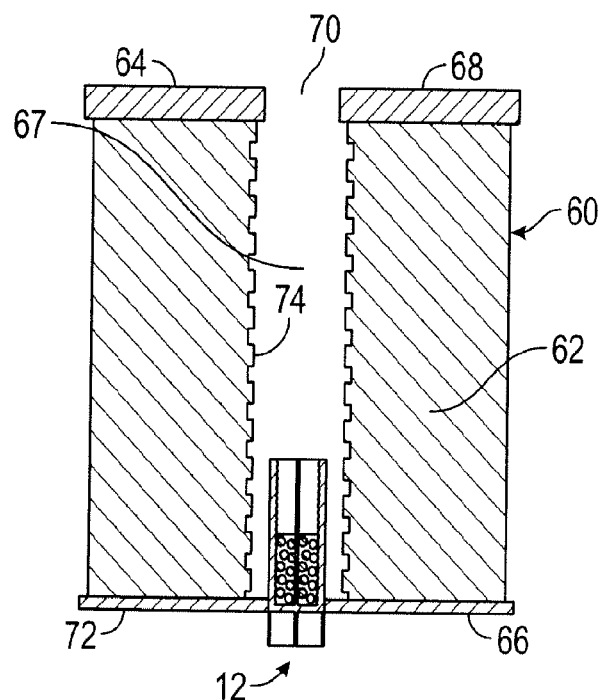
FIG. 3 illustrates the sensor probe of FIG. 2 incorporated into a cartridge filter element according to one embodiment.

FIG. 3 illustrates an example where the sensor probe 12 may be incorporated into a disposable filter element cartridge 60 that in use is removably disposed inside of a filter housing (not shown). The cartridge 60 together with the sensor probe 12 can be removed from the filter housing and replaced with a new cartridge containing the sensor probe.

The cartridge 60 can have many configurations depending upon its application. In the illustrated example, the cartridge 60 includes a closed loop of pleated filter media 62, generally cylindrical in shape, having a first axial end 64 and a second axial end 66 and defining a hollow interior space 67. At the first axial end 64 is an open endplate 68 that can be, for example, annular in shape and bonded to the end 64 of the media 62 using an appropriate adhesive or thermally bonded to the media. A hole 70 in the center of the endplate 68 enables fluid flow out of or into the interior space 67. The endplate 68 may provide structural support for the pleated filter media 62 and may seal at least one of the ends of the pleated filter media 62. Alternatively or additionally, the endplate 68 may provide a sealing surface for the filter cartridge to a filter head (not shown) or to the rest of the filter assembly. The endplate 68 may or may not include a compressible gasket or other sealing material to affect a seal. If the endplate 68 does not include a gasket or other sealing material, a gasket or other sealing material may be part of the corresponding mating housing/head structure.

A second, closed endplate 72 may be attached to the second axial end 66 of the media 62. The endplate 72 may be generally similar to the endplate 68, except that it lacks a flow hole. However, the endplate 72 may include a hole in which the sensor probe 12 is mounted and sealed to the endplate 72. The sensor probe 12 may protrude into the hollow interior space 67 where it is positioned to detect and measure the properties of the fluid. The electrical connector and the mounting protrusion 50 may protrude away from the endplate 72 in the opposite direction. The protrusion 50 may be of any design that enables the sensor probe 12 to communicate (directly via wires or indirectly using wireless communications) to the controller 22 such as an ECU or other signal processing or analysis unit. Examples of such connections are well known, such as those commonly used in the industry to connect water-in-fuel sensors used with fuel water separators to an engine's ECU. The protrusion 50 can further help to properly position the sensor probe 12 within the filter housing to ensure both proper sealing and electrical connection. An optional perforated center tube 74 can also be used that extends from the endplate 68 to the endplate 72 and that surrounds the interior cavity 67 to provide additional support, strength and rigidity to the media 62.

FIG. 4 illustrates an example where the sensor probe 12 may be incorporated into a disposable spin-on filter element 80 known in the art. The spin-on filter element 80 may include a filter cartridge 82 enclosed within a disposable shell or housing 84 that is open on one end. The open end may be closed by a threaded nutplate 86 with a central hole or opening 88 for fluid flow and typically a series of holes arranged annularly around the central hole for fluid flow in the reverse direction. The threaded nutplate 86 may be used to attach the spin-on filter to the mounting spud on the filter head. Gaskets or other sealing means may be used to seal the filter cartridge to the nutplate 86 and to ensure that the flow of fluid is directed through the filter media 90. Similar to the cartridge 60 in FIG. 3, the cartridge 82 may include an open endplate 92 at one end and an endplate 94 at the other end. In this example, a means 96 for introducing an additive into the fluid may be disposed between the endplate 94 and the closed end of the housing 84. A spring 98 may abut a bottom endplate 74 in order to bias the filter cartridge 82 against the nutplate 86. Further information on one type of spin-on filter element construction can be found in U.S. Pat. No. 5,906,736, the filter of which may include a funnel or venturi tube, or U.S. Pat. No. 7,510,653, the filter of which may be an additive release filter.

In FIG. 4, the sensing portion of the sensor probe 12 is illustrated as being disposed in an interior space of the housing 84 between the end of the filter cartridge 82 and the closed end of the housing 84, on the upstream side of the filter media to sense the fluid before the fluid is filtered. The sensor probe 12 may be secured to the closed end of the housing 84 in a manner that seals and does not leak and enables electrical connection to the controller 22 as discussed above for FIG. 3.

FIG. 5 illustrates another embodiment of a disposable spin-on filter element 100 known in the art that is modified to integrate the sensor probe 12. In this embodiment, the sensing portion of the sensor probe 12 may be positioned inside an interior space 102 of the filter media cylinder 104 similar to the embodiment shown in FIG. 3 on the downstream side of the filter media to sense the fluid after the fluid has been filtered. Similar to the cartridge 60 in FIG. 3, the cartridge may include an open endplate 106 at one end and a closed endplate 108 at the other end. In this embodiment, a coil spring 110 may act directly against the filter cartridge to bias the cartridge against the nutplate.

In lube and hydraulic oil applications, as oil degrades, the sensor probe 12 may produce an electronic output that can be utilized by the controller 22 to provide a real-time assessment of the oil quality. As the oil quality deteriorates, the chemically reactive material(s) of the sensor probe 12 undergoes reversible or irreversible chemical change if exposed to the chemical or contaminant specie(s) it is designed to monitor, which changes its electrical properties and thereby changes the electrical output of the sensor probe. (According to one embodiment, the sensor probe 12 may return to its base condition after a period of time or after certain processing.) At a predetermined threshold, both the probe 12 and the oil may be replaced as the probe 12 may no longer be usable for its intended purpose and the oil quality has degraded below a predetermined threshold. At the same time, the filter may also be replaced. Since the sensor probe 12 is part of the disposable filter element, the sensor probe may be replaced during each oil change along with the filter element. This ensures that spent sensor probes are replaced as required. An advantage of the sensor probe described herein is that it may not require recalibration, reinitialization, or a reset of the oil quality monitoring system when the sensor probe is replaced. Further, the cost, size and replaceable nature of the sensor probes facilitate their integration into the disposable filter element, enabling both disposable items (e.g. the filter element and the sensor probe) to be replaced simultaneously.

In fuel applications, much of the fuel is burned during combustion rather than recirculated. As a result, the properties of the fluid may vary due to the regular addition of new fluid (which may potentially have different properties). However, the comparison between the conductances across the two chambers 30a, 30b may dampen, lessen, or eliminate these fluctuations, allowing the critical species and/or parameters to be detected. In the case of water, the sensor probe may detect water concentration in the fuel.

According to another embodiment, the fluid filtration system may include a viscosity sensor for a more completely measure of the quality of the lubricant. The viscosity sensor may also produce an electronic output to provide real-time assessment of the oil quality (more specifically, of the oil viscosity). The viscosity sensor may be disposable or non-disposable. Further, the viscosity sensor may be positioned separately from the sensor probe or may be integral with the sensor probe. The viscosity sensor may be upstream or downstream from the filter element.

According to another embodiment, the sensor probe can be used to ensure that the correct filter is installed and/or to provide the broader engine system information concerning the filter. In this context, the sensor probe may be particularly useful when replacing, servicing, or repairing the filter in order to prevent an incorrect filter being installed within the fluid filtration system. Information from the sensor probe (which may be stored, for example, on an integrated circuit (IC) or a memory chip embedded therein) may be used by the engine control module (ECM) to identify or recognize the installed filter, shell, etc. based on electronic output of the sensor.

Figure 6:
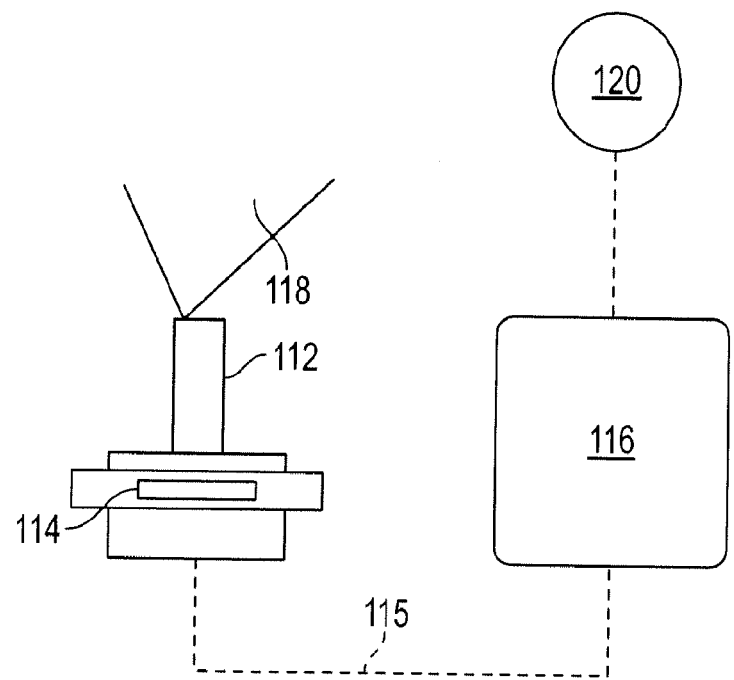
FIG. 6 is a schematic representation showing a sensor probe integrated into the filter assembly according to yet another embodiment.

FIG. 6 is a schematic representation showing a sensor probe 112 integrated into a filter assembly 118 according to this further embodiment. The sensor probe 112 includes a data storage and/or data processing unit 114 which may comprise an IC or memory chip embedded into the sensor probe 112. The data storage and/or data processing unit 114 may contain the details or the identity of the filter (e.g. a filter identification number, a filter batch number, etc.), information such as filter media's characteristics, and other information about the filter. The data storage and/or data processing unit 114 may also contain software or algorithms to process the raw data from the sensor probe 112 so as to indicate the quality of the fluid being filtered. This data may then be communicated to the engine control module (ECM) 116 via wires or wirelessly (as shown by dashed lines 115). This information can then be analyzed by the ECM to confirm if the filter is genuine and (if appropriate) to provide an indication 120 if the filter is not genuine.

It should be noted that the use of the sensor probe to provide identification information may be implemented independently of the chemically reactive material in certain embodiments. In other words, it is possible for identifying information to be provided in conjunction with the sensor probe without any fluid-sensitive chemically reactive materials being included anywhere on the filter.

In the situation where the sensor probe includes identifying information about the filter, the ECM may analyze this information in various contexts. For example, the ECM may use the identifying information to confirm that the correct or OEM-approved filter has been installed. Alternatively or additionally, the ECM could use the identifying information to determine the type of filter being used and, in response to this information, the ECM adjust the operation of the engine system as appropriate.

Still further, the very existence (or non-existence) of the sensor probe can be an indication of information concerning the appropriateness of the filter. In a particular arrangement, for example, the ECM can attempt to locate and identify the filter element based upon the expected information of the sensor probe. If the sensor probe is not present, then the ECM would recognize that the proper filter is not present. In response thereto, the ECM may communicate an indication 120 that the filter is not genuine. This indication 120 can be used to prevent the engine from operating, or otherwise restrict or limit the scope of the engine's operation, in order to reduce or prevent potential damage to the engine and associated components and systems.

The invention may be embodied in other forms without departing from the spirit or novel characteristics thereof. The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

It is anticipated that the various components, configurations, and features of the different embodiments of the sensor probe 12 may be combined according to the desired use and configuration.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

The invention claimed is:

1. A fluid filtration system comprising:
   a fluid filter assembly that includes a filter element configured to filter a fluid, the filter element comprising a first endplate, a second endplate, and filter media arranged in a cylindrical shape and positioned between the first endplate and the second endplate, the filter media defining a hollow interior space; and
   a sensor probe incorporated into the fluid filter assembly, the sensor probe comprising a probe portion and an electrical contact, the sensor probe mounted to the second endplate of the filter element such that the probe portion extends away from the second endplate and into the hollow interior space, wherein the sensor probe includes a chemically reactive material sensitive to at least one property of the fluid, wherein at least a portion of the sensor probe is exposed to the fluid.

2. The fluid filtration system of claim 1, wherein the at least one property includes at least one of a chemical concentration, a contaminant concentration, or a fluid parameter.

3. The fluid filtration system of claim 1, wherein the at least one property of the fluid changes at least one electrical property of the chemically reactive material.

4. The fluid filtration system of claim 3, wherein a real-time assessment of the at least one electrical property is provided by at least one of a signal processor or an engine control unit.

5. The fluid filtration system of claim 3, wherein changes in the at least one electrical property indicate at least one of a fluid quality, a fluid chemistry, or a chemical composition of the fluid.

6. The fluid filtration system of claim 5, wherein the fluid quality includes at least one of a soot level, fuel concentration, water concentration, or an extent of at least one of additive depletion, fluid oxidation, nitration, thermal degradation, liquid contamination, solid contamination, or semi-solid particulate contamination.

7. The fluid filtration system of claim 1, wherein the sensor probe is incorporated into at least one of the filter element, a filter head to which the filter element is attached, a filter housing in which the filter element is disposed, a sump, an engine lubricating fluid circuit, or a standpipe.

8. The fluid filtration system of claim 1, wherein the filter element is a spin-on filter element.

9. The fluid filtration system of claim 1, wherein the sensor probe is replaceable when at least one of the filter element or oil is changed.

10. The fluid filtration system of claim 9, wherein the sensor probe is not recalibrated after replacement.

11. The fluid filtration system of claim 1, wherein the sensor probe is positioned upstream from the filter element.

12. The fluid filtration system of claim 1, wherein the sensor probe is positioned downstream from the filter element.

13. The fluid filtration system of claim 1, further comprising a viscosity sensor configured to assess a viscosity of the fluid.

14. The fluid filtration system of claim 13, wherein the viscosity sensor is integral with the sensor probe.

15. The fluid filtration system of claim 13, wherein the viscosity sensor is separate from the sensor probe.

16. The fluid filtration system of claim 1, wherein the sensor probe is further configured to enable identification of the filter element.

17. The fluid filtration system of claim 1, wherein the sensor probe contains identifying information about the filter element.

18. The fluid filtration system of claim 1, wherein the electrical contact extends away from the second endplate in an opposite direction as the probe portion.

* * * * *

UNITED STATES PATENT AND TRADEMARK OFFICE
CERTIFICATE OF CORRECTION

PATENT NO. : 9,535,050 B2  
APPLICATION NO. : 14/899717  
DATED : January 3, 2017  
INVENTOR(S) : Jeffery A. Massey et al.

Page 1 of 1

It is certified that error appears in the above-identified patent and that said Letters Patent is hereby corrected as shown below:

On the Title Page

Item (72) Inventors:  
Delete "Jeffrey A. Massey" and insert therefor --Jeffery A. Massey--

Signed and Sealed this  
Twenty-eighth Day of March, 2017

Michelle K. Lee  
*Director of the United States Patent and Trademark Office*